(12) United States Patent
Hercouet et al.

(10) Patent No.: US 7,935,154 B2
(45) Date of Patent: May 3, 2011

(54) PROCESS FOR LIGHTENING OR LIGHTENING DIRECT DYEING OR OXIDATION DYEING IN THE PRESENCE OF AT LEAST ONE ORGANIC AMINE AND AT LEAST ONE INORGANIC BASE, AND DEVICE THEREFOR

(75) Inventors: Leïla Hercouet, Neuilly Plaisance (FR); Alain Lagrange, Coupvray (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 12/642,536

(22) Filed: Dec. 18, 2009

(65) Prior Publication Data
US 2010/0175705 A1    Jul. 15, 2010

Related U.S. Application Data

(60) Provisional application No. 61/151,612, filed on Feb. 11, 2009, provisional application No. 61/147,188, filed on Jan. 26, 2009.

(30) Foreign Application Priority Data

Dec. 19, 2008  (FR) ...................................... 08 07285
Dec. 19, 2008  (FR) ...................................... 08 07286

(51) Int. Cl.
*A61Q 5/10* (2006.01)
(52) U.S. Cl. ............. 8/405; 8/406; 8/407; 8/426; 8/431; 8/462; 8/463; 8/602; 8/604; 8/111; 132/202; 132/208
(58) Field of Classification Search ............... 8/405, 406, 8/407, 426, 431, 462, 463, 602, 604, 111; 132/202, 208
See application file for complete search history.

(56) References Cited

U.S. PATENT DOCUMENTS

| | | | |
|---|---|---|---|
| 3,100,739 A | | 8/1963 | Kaiser et al. |
| 3,369,970 A | | 2/1968 | McLaughlin et al. |
| 3,629,330 A | | 12/1971 | Brody et al. |
| 3,861,868 A | | 1/1975 | Milbrada |
| 4,138,478 A | | 2/1979 | Reese et al. |
| 4,170,637 A | | 10/1979 | Pum |
| 4,226,851 A | | 10/1980 | Sompayrac |
| 4,357,141 A | | 11/1982 | Grollier et al. |
| 4,366,099 A | | 12/1982 | Gaetani et al. |
| 4,488,564 A | | 12/1984 | Grollier et al. |
| 4,725,282 A | | 2/1988 | Hoch et al. |
| 4,845,293 A | | 7/1989 | Junino et al. |
| 5,021,066 A | | 6/1991 | Aeby et al. |
| 5,259,849 A | * | 11/1993 | Grollier et al. ................... 8/405 |
| 5,364,414 A | | 11/1994 | Lang et al. |
| 5,817,155 A | | 10/1998 | Yasuda et al. |
| 6,010,541 A | | 1/2000 | De La Mettrie et al. |
| 6,074,439 A | | 6/2000 | De La Mettrie et al. |
| 6,129,770 A | | 10/2000 | Deutz et al. |
| 6,156,713 A | | 12/2000 | Chopra et al. |
| 6,165,444 A | | 12/2000 | Dubief et al. |
| 6,190,421 B1 | | 2/2001 | Rondeau et al. |
| 6,206,935 B1 | | 3/2001 | Onitsuka et al. |
| 6,238,653 B1 | | 5/2001 | Narasimhan et al. |
| 6,251,378 B1 | | 6/2001 | Laurent et al. |
| 6,260,556 B1 | | 7/2001 | Legrand et al. |
| 6,277,154 B1 | | 8/2001 | Lorenz |
| 6,277,155 B1 | | 8/2001 | De La Mettrie et al. |
| 6,365,136 B1 | | 4/2002 | Lauscher et al. |
| 6,423,100 B1 | | 7/2002 | Lang et al. |
| 6,447,552 B1 | | 9/2002 | Golinski |
| 6,645,258 B2 | | 11/2003 | Vidal et al. |
| 6,660,045 B1 | | 12/2003 | Hoeffkes et al. |
| 6,695,887 B2 | | 2/2004 | Cottard et al. |
| 6,800,098 B1 | | 10/2004 | Allard et al. |
| 7,135,046 B2 | | 11/2006 | Audousset |
| 7,153,331 B2 | | 12/2006 | Desenne et al. |
| 7,217,298 B2 | | 5/2007 | Legrand et al. |
| 7,285,137 B2 | | 10/2007 | Vidal et al. |

(Continued)

FOREIGN PATENT DOCUMENTS

CA              1 268 421              5/1990

(Continued)

OTHER PUBLICATIONS

Database WPI Week 200470, Thomson Scientific, London, GB; AN 2004-711531, XP002491445.
French Search Report for FR 0807285, dated Sep. 28, 2009.
French Search Report for FR 0807286, dated Sep. 24, 2009.
English language abstract of DE 38 14 356 A1, Sep. 8, 1988.
English language abstract of FR 2 925 304 A1, Jun. 26, 2009.
English language abstract of FR 2 925 309 A1, Jun. 26, 2009.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.

(Continued)

*Primary Examiner* — Eisa B Elhilo
(74) *Attorney, Agent, or Firm* — Finnegan Henderson Farabow Garrett & Dunner, L.L.P.

(57) ABSTRACT

Provided is a process for lightening or dyeing keratin fibers, including human keratin fibers such as the hair, in the presence of an oxidizing agent, wherein the following are applied to the keratin fibers: (a) an anhydrous cosmetic composition (A) comprising at least one fatty substance and at least one surfactant, (b) a cosmetic composition (B) comprising at least one organic amine with a $pK_b$ of less than 12 at 25° C. and at least one mineral base, and (c) a composition (C) comprising at least one oxidizing agent; when the process described herein is a process for dyeing keratin fibers, composition (B) further comprises at least one dye. Also provided is a multi-compartment device comprising a first compartment having the anhydrous cosmetic composition, a second compartment having at least one organic amine with a $pK_b$ of less than 12 at 25° C., and also at least one mineral base and optionally at least one dye, and a third compartment having an oxidizing composition.

15 Claims, No Drawings

U.S. PATENT DOCUMENTS

| | | |
|---|---|---|
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard |
| 7,799,095 B2 | 9/2010 | Mario et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 A1 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 A1 | 1/2004 |
| EP | 1 430 873 A1 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 A2 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 034 A1 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 A1 | 6/2009 |
| FR | 2 925 307 | 6/2009 |
| FR | 2 925 308 | 6/2009 |
| FR | 2 925 309 A1 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |

| | | |
|---|---|---|
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 A2 | 7/2009 |
| WO | WO 2009/080668 | 7/2009 |
| WO | WO 2009/080669 | 7/2009 |
| WO | WO 2009/080670 A2 | 7/2009 |

OTHER PUBLICATIONS

Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 308, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2007/096497, dated Aug. 14, 2008.
English language Abstract of WO 91/11985, dated Aug. 22, 1991.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.

French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR LIGHTENING OR LIGHTENING DIRECT DYEING OR OXIDATION DYEING IN THE PRESENCE OF AT LEAST ONE ORGANIC AMINE AND AT LEAST ONE INORGANIC BASE, AND DEVICE THEREFOR

This application claims benefit of U.S. Provisional Application Nos. 61/147,188, filed Jan. 26, 2009, and 61/151,612, filed Feb. 11, 2009. This application also claims benefit of priority under 35 U.S.C. §119 to French Patent Application Nos. 0807285 and 0807286, filed Dec. 19, 2009.

Provided is a process for lightening or a process for dyeing keratin fibers, including human keratin fibers such as hair in the presence of at least one oxidizing agents, comprising the use of an anhydrous cosmetic composition (A) comprising at least one fatty substance and at least one surfactant, of a cosmetic composition (B) comprising at least one organic amine and at least one mineral base, and of an oxidizing composition (C) comprising at least one oxidizing agent, when the process described herein is a process for dyeing keratin fibers, the composition (B) may also comprise at least one dye.

Also provided is a multi-compartment device comprising a first compartment having the anhydrous cosmetic composition (A), a second compartment having the cosmetic composition (B) and a third compartment having an oxidizing composition (C).

For many years, people have sought to modify the color of their hair and to hide their grey hair. To do this, at least two types of coloration have been developed.

One type of coloration involves permanent dyeing or oxidation dyeing, using dye compositions comprising oxidation dye precursors, which may be known as oxidation bases. Those oxidation bases may be colorless or weakly colored compounds that, when combined with oxidizing products, can give rise, via a process of oxidative condensation, to colored compounds.

The shades obtained with those oxidation bases may often be varied by combining them with couplers or dye modifiers, which may be chosen from aromatic meta-diamines, meta-aminophenols, meta-diphenols, and heterocyclic compounds, such as indole compounds. The variety of molecules used as oxidation bases and couplers may allow a wide range of colors to be obtained.

Another type of dyeing involves semipermanent dyeing or direct dyeing, using dye compositions comprising direct dyes, which may comprise colored and coloring molecules having affinity for the fibers, leaving them on keratin fibers, for instance, for a time to allow the molecules to penetrate, by diffusion, into the fiber, and then rinsing them off. To perform those dyeing operations, the direct dyes were often chosen from nitrobenzene, anthraquinone, nitropyridine, azo, xanthene, acridine, azine, and triarylmethane direct dyes.

That type of process does not require using an oxidizing agent to develop the coloration. However, it is not excluded to use one to obtain a lightening effect along with the coloration. Such a process may then be referred to as a direct dyeing or semipermanent dyeing under lightening conditions.

Processes of lightening or of permanent or semipermanent dyeing under lightening conditions thus use, along with the dye composition, an aqueous composition comprising at least one oxidizing agent, under alkaline pH conditions. The role of that oxidizing agent is believed to be, at least in part, to degrade the melanin of the hair, which, depending on the nature of the oxidizing agent present, may lead to more or less pronounced lightening of the fibers. Thus, for relatively weak lightening, the oxidizing agent may be hydrogen peroxide. When more substantial lightening is desired, peroxygenated salts, for instance persulfates, may be used in the presence of hydrogen peroxide.

One of the difficulties encountered when implementing the lightening or lightening dyeing processes of the prior art may arise because those processes are performed under alkaline conditions and that the alkaline agent most commonly used is aqueous ammonia. Aqueous ammonia is believed to allow the pH of the composition to be adjusted to an alkaline pH to enable activation of the oxidizing agent. However, this alkaline agent also causes swelling of the keratin fiber, with raising of the scales, promoting the penetration of the oxidizing agent, and also of the dyes, for instance the oxidation dyes, into the fiber, increasing the efficacy of the dyeing reaction.

However, this alkaline agent is very volatile, which users find disagreeable due to the characteristic strong, rather unpleasant odor of ammonia that is given off during the process.

Furthermore, the amount of ammonia given off during the process makes it necessary to apply this alkaline agent in a larger amount than the amount required to form the process, to compensate for this loss. This is not without consequences on the user, who not only remains inconvenienced by the odor, but may also be confronted with greater risks of intolerance, for instance irritation of the scalp in the form, for instance, of stinging.

Replacing all or some of the aqueous ammonia with at least one other standard alkaline agents may lead to compositions that are less efficient than those based on aqueous ammonia, because those alkaline agents are not believed to afford sufficient lightening of pigmented fibers in the presence of the oxidizing agent.

Provided are lightening or dyeing processes of human keratin fibers performed in the presence of an oxidizing agent, which makes it possible to overcome at least one, and in certain embodiments all, of the aforementioned drawbacks.

Provided is a process for dyeing keratin fibers, including human keratin fibers such as the hair, in the presence of an oxidizing agent, in which the following are applied to said fibers:

(a) a cosmetic anhydrous composition (A) comprising at least one fatty substance and at least one surfactant;

(b) a cosmetic composition (B) comprising at least one organic amine whose $pK_b$ is less than 12 at 25° C. and at least one inorganic base; and (c) a composition (C) comprising at least one oxidizing agent; and when the process described herein is a process for dyeing keratin fibers, the composition (B) also comprises at least one oxidation dye, at least one direct dye, or both.

The dyeing process described herein, in some embodiments, may lead to strong, sparingly selective colorations, i.e. colorations that are uniform along the fiber.

Moreover, the processes described herein may make it possible, in some embodiments, to produce compositions that do not give off an aggressive odor when they are applied to the hair or during their preparation.

Also provided is a multi-compartment device comprising, in a first compartment, an anhydrous cosmetic composition (A) comprising at least one fatty substance and at least one surfactant, in a second compartment, a cosmetic composition (B) comprising at least one organic amine with a $pK_b$ of less than 12 at 25° C. and at least one mineral base, and also optionally at least one oxidation dye and/or at least one direct dye, and, in a third compartment, a composition (C) comprising at least one oxidizing agent.

Also provided is an anhydrous composition comprising at least one fatty substance, at least one surfactant, at least one organic amine with a $pK_b$ of less than 12 at 25° C., and at least one mineral base other than aqueous ammonia.

Other characteristics and advantages of the invention will emerge more clearly on reading the description and the examples that follow.

In the text hereinbelow, and unless otherwise indicated, the limits of a range of values are included in that range.

In some embodiments, the human keratin fibers treated by the process described herein are human hair.

In some embodiments, the dyeing process described herein is performed in the presence of a cosmetic anhydrous composition (A).

In some embodiments, the term "cosmetic anhydrous composition" means a cosmetic composition with a water content of zero or less than 5% by weight. In some embodiments, the term "cosmetic anhydrous composition" means a cosmetic composition with a water content of zero or less than 2% by weight. In some embodiments, the term "cosmetic anhydrous composition" means a cosmetic composition with a water content of zero or less than 1% by weight. In some embodiments, the water of crystallization of salts or traces of water absorbed by the starting materials used in the preparation of the compositions described herein.

In some embodiments, the lightening process described herein is performed in the presence of compositions not comprising a direct dye or an oxidation dye precursor (bases and couplers). In some embodiments, the lightening process is performed in the presence of compositions comprising a direct dye or an oxidation dye precursor (bases and couplers), whose total content is less than 0.005% by weight relative to the weight of each of the compositions. At such a content, only the composition would be eventually dyed, i.e. no coloration of the keratin fibers would be observed.

In some embodiments, the lightening process described herein is performed without oxidation base, coupler, or direct dye.

The at least one fatty substance describes an organic compound that is insoluble in water at ordinary ambient temperature (25° C.) and at atmospheric pressure (760 mmHg). In some embodiments, the at least one fatty substance has a water solubility of less than 5%. In some embodiments, the at least one fatty substance has a water solubility of less than 1%. In some embodiments, the at least one fatty substance has a water solubility of less than 0.1%. In some embodiments, the at least one fatty substance has a structure with at least one hydrocarbon chain comprising at least two siloxane groups. In some embodiments, the at least one fatty substance is soluble in organic solvents under the same temperature and pressure conditions, for instance chloroform, ethanol, benzene, liquid petroleum jelly, and decamethyl cyclopentasiloxane.

Exemplary fatty substances include, but are not limited to, $C_6$-$C_{16}$ lower alkanes, non-silicone animal, plant, mineral or synthetic oils, fatty alcohols, fatty acids, esters of a fatty acid and/or of a fatty alcohol, nonsilicone waxes, and silicones.

In some embodiments, the fatty alcohols, fatty esters, and fatty acids comprise at least one linear or branched, saturated or unsaturated hydrocarbon-based group having 6 to 30 carbon atoms, which is optionally substituted, with at least one hydroxyl group. If they are unsaturated, those compounds may comprise one to three conjugated or nonconjugated carbon-carbon double bonds.

In some embodiments, the lower $C_6$-$C_{16}$ alkanes are linear. In some embodiments, the lower $C_6$-$C_{16}$ alkanes are branched. In some embodiments, the lower $C_6$-$C_{16}$ alkanes are cyclic. By way of non-limiting example, the lower $C_6$-$C_{16}$ alkanes may be chosen from hexane, undecane, dodecane, tridecane, and isoparaffins (for instance isohexadecane and isodecane).

Exemplary non-silicone oils that may be used in the compositions described herein include, but are not limited to:

hydrocarbon-based oils of animal origin, such as perhydrosqualene;

triglycerides of plant or synthetic origin, such as liquid fatty acid triglycerides having from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, having more than 16 carbon atoms, such as volatile or nonvolatile liquid paraffins, and derivatives thereof, petroleum jelly, liquid petroleum jelly, polydecenes, hydrogenated polyisobutene such as PARLEAM®, liquid paraffins, liquid petroleum jelly, petroleum jelly, polydecenes, hydrogenated polyisobutene such as PARLEAM®;

partially hydrocarbon-based fluoro oils that may also be mentioned include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

Exemplary fatty alcohols that may be used in the anhydrous cosmetic composition (A) include, but are not limited to, linear or branched, saturated or unsaturated fatty alcohols having from 6 to 30 carbon atoms or from 8 to 30 carbon atoms, for instance cetyl alcohol, stearyl alcohol, and the mixture thereof (cetylstearyl alcohol), octyldodecanol, 2-butyloctanol, 2-hexyldecanol, 2-undecylpentadecanol, oleyl alcohol, and linoleyl alcohol.

Exemplary waxes that may be used in the anhydrous cosmetic composition (A) include, but are not limited to, carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); marine waxes such as the product sold by the company Sophim under the reference M82, polyethylene waxes, and polyolefin waxes.

Exemplary fatty acids that may be used in the anhydrous cosmetic composition (A) include, but are not limited to, saturated or unsaturated and have from 6 to 30 carbon atoms or 9 to 30 carbon atoms, myristic acid, palmitic acid, stearic acid, behenic acid, oleic acid, linoleic acid, linolenic acid, and isostearic acid.

Exemplary esters of fatty acid and/or of fatty alcohol include, but are not limited to, the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols. In some embodiments, the total carbon number of the esters is greater than or equal to 10.

Exemplary monoesters include, but are not limited to octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate; hexyl stearate, butyl stearate, isobutyl stearate; dioctyl malate, hexyl laurate, and 2-hexyldecyl laurate.

Other exemplary esters include, but are not limited to, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

Other exemplary esters include, but are not limited to: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; polyethylene glycol distearates ethyl, isopropyl, myristyl, cetyl or stearyl palmitate; 2-ethylhexyl palmitate; 2-octyldecyl palmitate; alkyl myristates such as isopropyl, butyl, cetyl or 2-octyldodecyl myristate; hexyl stearate, butyl stearate; isobutyl stearate; dioctyl malate; hexyl laurate; 2-hexyldecyl laurate; isononyl isononanoate; and cetyl octanoate.

The compositions described herein may further comprise, as fatty ester, sugar esters and diesters of $C_6$-$C_{30}$ or $C_{12}$-$C_{22}$ fatty acids. The term "sugar" includes oxygen-bearing hydrocarbon-based compounds having several alcohol functions, with or without aldehyde or ketone functions, and having at least 4 carbon atoms. Those sugars may be monosaccharides, oligosaccharides, or polysaccharides.

Exemplary sugars include, but are not limited to, sucrose (or saccharose), glucose, galactose, ribose, fucose, maltose, mannose, arabinose, xylose, and lactose, and derivatives thereof, including alkyl derivatives, such as methyl derivatives, for instance methylglucose.

In some embodiments, the sugar esters of fatty acids may be chosen from the group comprising the esters or mixtures of esters of sugars described previously and of linear or branched, saturated or unsaturated $C_6$-$C_{30}$ fatty acids. If they are unsaturated, those compounds may comprise, in some embodiments, one to three conjugated or nonconjugated carbon-carbon double bonds.

Exemplary esters may also include, but are not limited to, mono-, di-, tri-, tetraesters and polyesters, and mixtures thereof.

Exemplary esters may also include, but are not limited to, laurates, palmitates, myristates, behenates, cocoates, stearates, linoleates, linolenates, caprates and arachidonates, or mixtures thereof such as, such as, oleo-palmitate, oleo-stearate, and palmito-stearate mixed esters.

In some embodiments, monoesters and diesters and for example sucrose, glucose or methylglucose mono- or dioleates, stearates, behenates, oleopalmitates, linoleates, linolenates, and oleostearates may also be used.

An example that may be mentioned, in a nonlimiting manner, is the product sold under the name GLUCATE® DO by the company Amerchol, which is a methylglucose dioleate.

Exemplary esters or mixtures of esters of sugar and of fatty acid include, but are not limited to:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% di-triester-polyester;

the sucrose mono-dipalmito-stearate sold by the company Goldschmidt under the name TEGOSOFT® PSE.

In some embodiments, the silicones that may be used in the anhydrous cosmetic composition (A) described herein are volatile or nonvolatile, cyclic, linear or branched silicones, which are unmodified or modified with organic groups, having a viscosity from $5 \times 10^{-6}$ to 2.5 m$^2$/s at 25° C.

In some embodiments, the silicones that may be used in compositions described herein may be in the form of oils, waxes, resins, or gums.

Exemplary silicones include, but are not limited to, polydialkylsiloxanes, such as polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968) Academic Press. They can be volatile or nonvolatile.

Exemplary volatile silicones include, but are not limited to, those having a boiling point ranging from 60° C. to 260° C., including:

(i) cyclic polydialkylsiloxanes having from 3 to 7 or 4 to 5 silicon atoms, such as octamethylcyclotetrasiloxane sold under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Mention, in a nonlimiting manner, may also be made of cyclocopolymers of the dimethylsiloxane/methylalkylsiloxane type, such as VOLATILE SILICONE® FZ 3109 sold by the company Union Carbide, of formula:

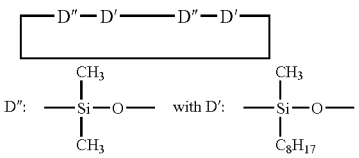

Mention, in a nonlimiting manner, may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane.

Exemplary volatile silicones also include (ii) linear volatile polydialkylsiloxanes having 2 to 9 silicon atoms and having a viscosity of less than or equal to $5 \times 10^{-6}$ m$^2$/s at 25° C. An example is decamethyltetrasiloxane sold for instance under the name SH 200 by the company Toray Silicone. Silicones belonging to this category are also described in the article published in COSMETICS AND TOILETRIES, Vol. 91, January 76, pp. 27-32, Todd & Byers "Volatile Silicone Fluids for Cosmetics."

In some embodiments, nonvolatile polydialkylsiloxanes, polydialkylsiloxane gums and resins, polyorganosiloxanes modified with organofunctional groups above, and mixtures thereof, may be used.

Exemplary silicones include, but are not limited to, polydialkylsiloxanes, such as polydimethylsiloxanes having trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60 000 mm$^2$/s;

the VISCASIL® oils from General Electric and certain oils of the SF series (SF 96, SF 18) from General Electric.

Mention, in a nonlimiting manner, may also be made of polydimethylsiloxanes having dimethylsilanol end groups known under the name dimethiconol (CTFA), such as the oils of the 48 series from the company Rhodia.

In this category of polydialkylsiloxanes, mention, in a nonlimiting manner, may also be made of the products sold under the names ABIL WAX® 9800 and 9801 by the company Goldschmidt, which are poly($C_1$-$C_{20}$)dialkylsiloxanes.

Exemplary silicone gums include, but are not limited to, polydialkylsiloxanes, such as polydimethylsiloxanes with high number-average molecular masses ranging from 200,000 to 1,000,000, used alone or as a mixture in a solvent. In some embodiments, this solvent can be chosen from volatile silicones, polydimethylsiloxane (PDMS) oils, poly-phenylmethylsiloxane (PPMS) oils, isoparaffins, polyisobutylenes, methylene chloride, pentane, dodecane, tridecane, and mixtures thereof.

Exemplary mixtures include, but are not limited to:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500 000, dissolved in the oil SF 1202 SILICONE FLUID corresponding to decamethylcyclopentasiloxane;

mixtures of two PDMSs with different viscosities, including mixtures of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may comprise 15% SE 30 gum and 85% SF 96 oil.

The organopolysiloxane resins include, but are not limited to, crosslinked siloxane systems having the following units:

$(R)_2SiO_{2/2}$, $(R)_3SiO_{1/2}$, $(R)SiO_{3/2}$ and $SiO_{4/2}$ in which R represents a hydrocarbon-based group having 1 to 16 carbon atoms. In some embodiments, R denotes a $C_1$-$C_4$ lower alkyl radical, such as methyl.

Among those resins, mention, in a nonlimiting manner, may be made of the product sold under the name DOW CORNING 593 or those sold under the names SILICONE FLUID SS 4230 and SS 4267 by the company General Electric, which are silicones of dimethyl/trimethyl siloxane structure.

Mention, in a nonlimiting manner, may also be made of the trimethyl siloxysilicate type resins sold for instance under the names X22-4914, X21-5034, and X21-5037 by the company Shin-Etsu.

In some embodiments, the organomodified silicones are silicones described above and comprising in their structure at least one organofunctional group attached via a hydrocarbon-based radical.

Besides the silicones described above, in some embodiments, the organomodified silicones may be polydiarylsiloxanes, including polydiphenylsiloxanes, and polyalkylarylsiloxanes functionalized with organofunctional groups.

In some embodiments, the polyalkylarylsiloxanes may be chosen from linear and/or branched polydimethyl/methylphenylsiloxanes and polydimethyl/diphenylsiloxanes with a viscosity of from $1 \times 10^{15}$ to $5 \times 10^{-2}$ m$^2$/s at 25° C.

Exemplary polyalkylarylsiloxanes include, but are not limited to, the products sold under the following names:

the SILBIONE® oils of the 70 641 series from Rhodia;

the oils of the RHODOURSIL® 70 633 and 763 series from Rhodia;

the oil DOW CORNING 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250, and SF 1265.

Among the organomodified silicones, mention may be made, in a nonlimiting manner, of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;

alkoxylated groups such as the product sold under the name SILICONE COPOLYMER F-755 by SWS Silicones, and ABIL WAX® 2428, 2434 and 2440 by the company Goldschmidt.

In some embodiments, the at least one fatty substance does not comprise any $C_2$-$C_3$ oxyalkylene units or any glycerolated units.

In some embodiments, the at least one fatty substance is chosen from compounds that are liquid or pasty at room temperature and at atmospheric pressure.

In some embodiments, the at least one fatty substance is not a fatty acid.

In some embodiments, the at least one fatty substance is chosen from $C_6$-$C_{16}$ lower alkanes, non-silicone mineral, plant or synthetic oils, fatty alcohols, esters of a fatty acid and/or of a fatty alcohol, and silicones.

In some embodiments, the at least one fatty substance is not silicone.

In some embodiments, the at least one fatty substance is chosen from liquid petroleum jelly, polydecenes, fatty acid and/or fatty alcohol esters, liquid esters, or mixtures thereof.

In some embodiments, the anhydrous cosmetic composition (A) comprises a fatty substance content ranging from 10% to 99% by weight relative to the weight of the anhydrous composition (A). In some embodiments, the anhydrous cosmetic composition (A) comprises a fatty substance content ranging from 20% to 90% by weight relative to the weight of the anhydrous composition (A). In some embodiments, the anhydrous cosmetic composition (A) comprises a fatty substance content ranging from 25% to 80% by weight relative to the weight of the anhydrous composition (A).

In some embodiments, the anhydrous cosmetic composition (A) also comprises at least one surfactant.

In some embodiments, the at least one surfactant is chosen from nonionic surfactants and anionic surfactants.

Exemplary anionic surfactants include, but are not limited to, the salts (including alkali metal salts, such as sodium salts, ammonium salts, or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, such as those having from 2 to 50 ethylene oxide groups;

and mixtures thereof.

In some embodiments, the alkyl or acyl radical of those various compounds may have from 6 to 24 carbon atoms or from 8 to 24 carbon atoms, and the aryl radical may denote a phenyl or benzyl group.

Exemplary nonionic surfactants include, but are not limited to, monooxyalkylenated or polyoxyalkylenated, monoglycerolated or polyglycerolated nonionic surfactants. The oxyalkylene units may be oxyethylene or oxypropylene units, or a combination thereof. In some embodiments, the oxyalkylene units are oxyethylene units.

Examples of oxyalkylenated nonionic surfactants that may be mentioned, in a nonlimiting manner, include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, condensates of ethylene oxide and/or of propylene oxide, inter glia, or mixtures thereof.

In some embodiments, the at least one surfactant comprise a number of moles of ethylene oxide and/or of propylene oxide ranging from 1 to 100 or ranging from 2 to 50. In some embodiments, the nonionic surfactants do not comprise any oxypropylene units.

In some embodiments, the oxyalkylenated nonionic surfactants are chosen from oxyethylenated $C_8$-$C_{30}$ alcohols, polyoxyethylenated linear or branched, saturated or unsaturated $C_8$-$C_{30}$ acid esters, and polyoxyethylenated sorbitol esters.

As examples of monoglycerolated or polyglycerolated nonionic surfactants, monoglycerolated or polyglycerolated $C_8$-$C_{40}$ alcohols may be used.

In some embodiments, the monoglycerolated or polyglycerolated $C_8$-$C_{40}$ alcohols correspond to the following formula:

RO—[CH$_2$—CH(CH$_2$OH)—O]$_m$—H in which R represents a linear or branched $C_8$-$C_{40}$ alkyl or alkenyl radical, and m represents a number ranging from 1 to 30. In some embodiments, m represents a number ranging from 1 to 10.

Exemplary compounds that are suitable for use in the compositions described herein include, but are not limited to, lauryl alcohol having 4 mol of glycerol (INCI name: Polyglyceryl-4 Lauryl Ether), lauryl alcohol having 1.5 mol of glycerol, oleyl alcohol having 4 mol of glycerol (INCI name: Polyglyceryl-4 Oleyl Ether), oleyl alcohol having 2 mol of glycerol (INCI name: Polyglyceryl-2 Oleyl Ether), cetearyl alcohol having 2 mol of glycerol, cetearyl alcohol having 6 mol of glycerol, oleocetyl alcohol having 6 mol of glycerol, and octadecanol having 6 mol of glycerol.

In some embodiments, the alcohol may represent a mixture of alcohols in the same way that the value of m represents a statistical value, which means that, in a commercial product, several species of polyglycerolated fatty alcohol may coexist in the form of a mixture.

In some embodiments, among the monoglycerolated or polyglycerolated alcohols the $C_8$/$C_{10}$ alcohol having 1 mol of glycerol, the $C_{10}$/$C_{12}$ alcohol having 1 mol of glycerol and the $C_{12}$ alcohol having 1.5 mol of glycerol may be used.

In some embodiments, the at least one surfactant present in the anhydrous composition is a nonionic surfactant.

In some embodiments, the at least one surfactant is present in the anhydrous composition (A) in an amount ranging from 0.1% to 50% by weight relative to the weight of the anhydrous composition. In some embodiments, the at least one surfactant is present in the anhydrous composition (A) in an amount ranging from 0.5% to 30% by weight relative to the weight of the anhydrous composition. In some embodiments, the anhydrous composition (A) may also comprise at least one adjuvant, such as anionic, cationic, nonionic, amphoteric or zwitterionic polymers, or mixtures thereof; mineral thickeners, and fillers such as clays, talc; organic thickeners with, for instance, anionic, cationic, nonionic and amphoteric polymeric associative thickeners other than the polymers mentioned above; antioxidants; penetrants; sequestrants; fragrances; dispersants; film-forming agents; ceramides; preserving agents; and opacifiers.

In some embodiments, the at least one adjuvant is present in an amount ranging from 0.01% to 20% by weight relative to the weight of composition (A).

In some embodiments, the anhydrous composition (A) comprises at least one mineral thickener chosen from organophilic clays, fumed silicas, or mixtures thereof.

Exemplary organophilic clays include, but are not limited to, montmorillonite, bentonite, hectorite, attapulgite and sepiolite, and mixtures thereof. In some embodiments, the clay is a bentonite or a hectorite.

In some embodiments, the clay is modified with a chemical compound chosen from quaternary amines, tertiary amines, amine acetates, imidazolines, amine soaps, fatty sulfates, alkyl aryl sulfonates, amine oxides, and mixtures thereof.

Organophilic clays that may be mentioned, in a nonlimiting manner, include quaternium-18 bentonites such as those sold under the names BENTONE 3, BENTONE 38, and BENTONE 38V by the company Rheox, TIXOGEL VP by the company United Catalyst, CLAYTONE 34, CLAYTONE 40, and CLAYTONE XL by the company Southern Clay; stearalkonium bentonites such as those sold under the names BENTONE 27 by the company Rheox, TIXOGEL LG by the company United Catalyst and CLAYTONE AF and Claytone APA by the company Southern Clay; quaternium-18/benzalkonium bentonites such as those sold under the names CLAYTONE HT and CLAYTONE PS by the company Southern Clay; quaternium-18 hectorites such as those sold under the names BENTONE GEL DOA, BENTONE GEL ECO5, BENTONE GEL EUG, BENTONE GEL IPP, BENTONE GEL ISD, BENTONE GEL SS71, BENTONE GEL VS8, and BENTONE GEL VS38 by the company Rheox, and SIMAGEL M and SIMAGEL SI 345 by the company Biophil.

In some embodiments, the fumed silicas may be obtained by high-temperature hydrolysis of a volatile silicon compound in an oxhydric flame, producing a finely divided silica. This process may make it possible to obtain hydrophilic silicas having a large number of silanol groups at their surface. Such hydrophilic silicas are sold, for example, under the names AEROSIL 130®, AEROSIL 200®, AEROSIL 255®, AEROSIL 300®, and AEROSIL 380® by the company Degussa, and CAB-O-SIL HS-5®, CAB-O-SIL EH-5®, CAB-O-SIL LM-130®, CAB-O-SIL MS-55®, and CAB-O-SIL M-5® by the company Cabot.

It may be possible to chemically modify the surface of the silica via chemical reaction to reduce the number of silanol groups. In some embodiments, silanol groups are substituted with hydrophobic groups: a hydrophobic silica is then obtained.

The hydrophobic groups may include, but are not limited to:

trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references AEROSIL R812® by the company Degussa and CAB-O-SIL TS-530® by the company Cabot.

dimethylsilyloxyl or polydimethylsiloxane groups, which may be obtained by treating fumed silica in the presence of polydimethylsiloxane or dimethyldichlorosilane. Silicas thus treated are known as "Silica dimethyl silylate" according to the CTFA (6th edition, 1995). They are sold, for example, under the references AEROSIL R972®, and AEROSIL R974® by the company Degussa, and CAB-O-SIL TS-610® and CAB-O-SIL TS-720® by the company Cabot.

In some embodiments, the fumed silica may have a particle size that may be nanometric to micrometric, for example ranging from about 5 to 200 nanometers.

In some embodiments, the composition comprises a hectorite, an organomodified bentonite or a fumed silica. In some embodiments, the composition is modified.

In some embodiments, the composition additionally comprises at least one mineral thickener presents in an amount ranging from 1% to 30% by weight relative to the weight of the composition.

In some embodiments, the composition is in the form of a gel or a cream.

In some embodiments, the lightening process described herein is performed in the presence of composition (B) that does not comprise any direct dye or oxidation dye precursor (bases and couplers). In some embodiments, the lightening process is performed in the presence of compositions comprising a direct dye or an oxidation dye precursor (bases and couplers), whose total content is less than 0.005% by weight relative to the weight of composition (B). In some embodiments, the lightening process is performed without oxidation base, coupler, or direct dye.

In some embodiments, the dyeing process described herein is performed in the presence of a cosmetic composition (B) comprising at least one oxidation dye, at least one direct dye, or mixtures thereof.

In some embodiments, the oxidation dyes may be chosen from at least one oxidation base that may be combined with at least one coupler.

Exemplary oxidation bases include, but are not limited to, para-phenylenediamines, bis(phenyl)alkylenediamines, para-aminophenols, ortho-aminophenols and heterocyclic bases, and the addition salts thereof.

Among the para-phenylenediamines that may be mentioned, in a nonlimiting manner, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)-amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the bis(phenyl)alkylenediamines that may be mentioned, in a nonlimiting manner, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylene-diamine, N,N'-bis (ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, in a nonlimiting manner, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, in a nonlimiting manner, are 2-aminophenol, 2-amino-5-methylphenol, 2-amino-6-methylphenol and 5-acetamido-2-aminophenol, and the addition salts thereof.

Among the heterocyclic bases that may be mentioned, in a nonlimiting manner, are pyridine derivatives, pyrimidine derivatives and pyrazole derivatives.

Among the pyridine derivatives that may be mentioned, in a nonlimiting manner, are the compounds described, for example, in patents GB 1 026 978 and GB 1 153 196, for instance 2,5-diaminopyridine, 2-(4-methoxyphenyl)amino-3-amino-pyridine and 3,4-diaminopyridine, and the addition salts thereof.

Other pyridine oxidation bases that may be used include the 3-aminopyrazolo[1,5-a]pyridine oxidation bases or addition salts thereof described, for example, in patent application FR 2 801 308. Examples that may be mentioned include, but are not limited to, pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned, in a nonlimiting manner, are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned, in a nonlimiting manner, are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof. 4,5-Diamino-1-(β-methoxyethyl)pyrazole may also be used.

In some embodiments, a 4,5-diaminopyrazole is used. In some embodiments, a 4,5-diamino-1-(β-hydroxyethyl)pyrazole and/or a salt thereof is used.

Pyrazole derivatives that may also be mentioned, in a nonlimiting manner, include diamino-N,N-dihydropyrazolopyrazolones, and those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H, 5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo [1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a] pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

In some embodiments, 2,3-diamino-6,7-dihydro-1H,5H-pyrazolo[1,2-a]pyrazol-1-one and/or a salt thereof is used.

In some embodiments, 4,5-diamino-1-(β-hydroxyethyl) pyrazole and/or 2,3-diamino-6,7-dihydro-1H,5H-pyrazolo [1,2-a]pyrazol-1-one and/or a salt thereof may be used as heterocyclic bases.

In some embodiments, the cosmetic composition (B) may optionally comprise at least one coupler.

Among those couplers, mention, in a nonlimiting manner, may be made of meta-phenylenediamines, meta-aminophenols, meta-diphenols, naphthalene-based couplers, heterocyclic couplers, and also the addition salts thereof.

Mention, in a nonlimiting manner, may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)1-methoxy-benzene, 1,3-diaminobenzene, 1,3-bis(2, 4-diaminophenoxy)propane, 3-ureidoaniline, 3-ureido-1-dimethylaminobenzene, sesamol, 1-β-hydroxyethylamino-3, 4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a] benzimidazole, the addition salts thereof with an acid, and mixtures thereof.

In some embodiments, the addition salts of the oxidation bases and couplers may be chosen from the addition salts with an acid such as the hydrochlorides, hydrobromides, sulfates, citrates, succinates, tartrates, lactates, tosylates, benzenesulfonates, phosphates, and acetates.

In some embodiments, the oxidation bases are each present in an amount ranging from 0.0001% to 10% by weight relative to the total weight of the composition. In some embodiments, the oxidation bases are each present in an amount ranging from 0.005% to 5% by weight relative to the total weight of the composition.

In some embodiments, the couplers are each present in an amount ranging from 0.0001% to 10% by weight relative to the total weight of the composition. In some embodiments, the couplers are each present in an amount ranging from 0.005% to 5% by weight relative to the total weight of the cosmetic composition (B).

As regards the direct dyes, those dyes may be chosen from ionic and nonionic species. In some embodiments, the dyes are chosen from cationic and nonionic species.

Examples of suitable direct dyes that may be mentioned, in a nonlimiting manner, include azo; methine; carbonyl; azine; nitro (hetero)aryl; tri(hetero)arylmethane; porphyrin; phthalocyanin direct dyes, and natural direct dyes, alone or as mixtures.

In some embodiments, the azo dyes comprise an —N═N— function, the two nitrogen atoms of which are not simultaneously engaged in a ring. However, it is not excluded for one of the two nitrogen atoms of the sequence —N═N— to be engaged in a ring.

The dyes of the methine family may be, in some embodiments, compounds comprising at least one sequence chosen from >C═C< and —N═C<, the two atoms of which are not simultaneously engaged in a ring. However, it is pointed out that one of the nitrogen or carbon atoms of the sequences may be engaged in a ring. In some embodiments, the dyes of this family are derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include, but are not limited to: dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention, in a nonlimiting manner, may be made of azine, xanthene, thioxanthene, fluorindine, acridine, (di)oxazine, (di)thiazine and pyronin.

In some embodiments, the nitro (hetero)aromatic dyes may be chosen from nitrobenzene or nitropyridine direct dyes.

As regards the dyes of porphyrin or phthalocyanin type, it is possible to use cationic or noncationic compounds, optionally in some embodiments, comprising at least one metal or metal ion, for instance alkali metals, alkaline-earth metals, zinc, and silicon.

Exemplary direct dyes that may be mentioned, in a nonlimiting manner, include nitrobenzene dyes; azo direct dyes; azomethine direct dyes; methine direct dyes; azacarbocyanin direct dyes, for instance tetraazacarbocyanins (tetraazapentamethines); quinone and in some embodiments, anthraquinone, naphthoquinone or benzoquinone direct dyes; azine; xanthene; triarylmethane; indoamine; indigoid; phthalocyanin direct dyes, porphyrins and natural direct dyes, alone or as mixtures.

In some embodiments, these dyes may be monochromophoric dyes (i.e. comprising only one dye) or polychromophoric, including di- or trichromophoric; the chromophores possibly being identical or different, and from the same chemical family or otherwise. In some embodiments, the polychromophoric dye may comprise several radicals each derived from a molecule that absorbs in the visible region ranging from 400 to 800 nm. Furthermore, in some embodiments, this absorbance of the dye may not require any prior oxidation thereof, or combination with any other chemical species.

In the case of polychromophoric dyes, in some embodiments, the chromophores may be connected together by means of at least one linker, which may be cationic or noncationic.

In some embodiments, the linker is a linear, branched or cyclic $C_1$-$C_{20}$ alkyl chain, optionally interrupted with at least one heteroatom (such as nitrogen or oxygen) and/or with at least one group comprising such an atom ($CO$, $SO_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or perm groups.

If the heterocycles or aromatic nuclei are substituted, in some embodiments, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing at least one hydroxyl group.

Among the benzenic direct dyes, mention may be made in a nonlimiting manner of the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl) aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene 1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methane, and tetraazapentamethine direct dyes, mention, in a nonlimiting manner, may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, mention, in a nonlimiting manner, may be made of the following dyes of formulae (I) to (IV), and the compounds of formulae (I) and (III):

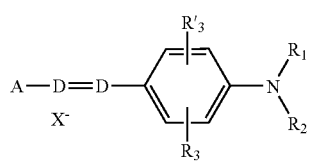
(I)

in which:

D represents a nitrogen atom or a —CH group, $R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, a heterocycle optionally having oxygen or nitrogen, which may be substituted with at least one $C_1$-$C_4$ alkyl radical; a 4'-aminophenyl radical, $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy, or acetyloxy radical, $X^-$ represents an anion that may be chosen from chloride, methyl sulfate and acetate, A represents a group chosen from structures A1 to A18, below:

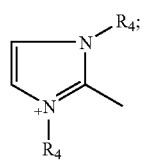
A$_1$

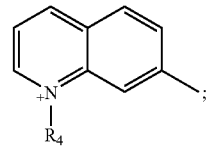
A$_2$

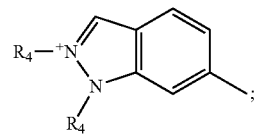
A$_3$

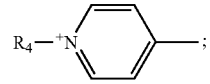
A$_4$

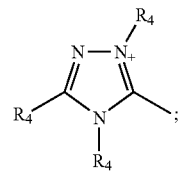
A$_5$

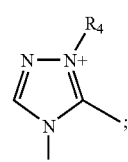
A$_6$

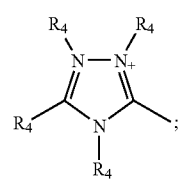
A$_7$

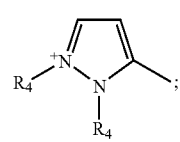
A$_8$

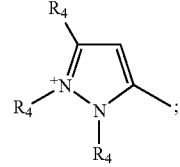
A$_9$

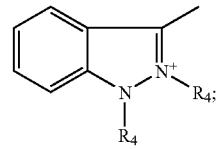
A$_{10}$

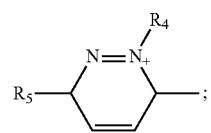
A$_{11}$

-continued

A12 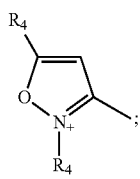

A13 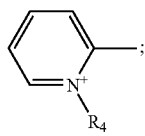

A14 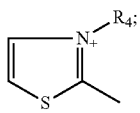

A15 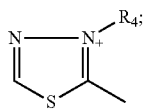

A16 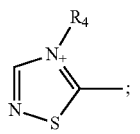

A17 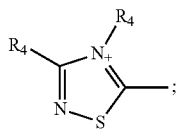

A18 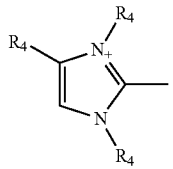

in which $R_4$ represents a $C_1$-$C_4$ alkyl radical, which may be substituted with a hydroxyl radical and $R_5$ represents a $C_1$-$C_4$ alkoxy radical;

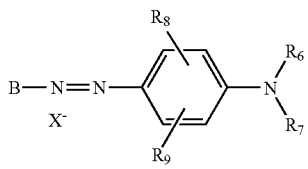
(II)

in which:
$R_6$ represents a hydrogen atom or a $C_1$-$C_4$ alkyl radical,
$R_7$ represents a hydrogen atom, an alkyl radical, which may be substituted with a —CN radical or with an amino group, a 4'-aminophenyl radical, or forms with $R_6$ a heterocycle optionally having oxygen and/or nitrogen, which may be substituted with a $C_1$-$C_4$ alkyl radical,
$R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, or a —CN radical, $X^-$ represents an anion that may be chosen from chloride, methyl sulfate, and acetate,
B represents a group chosen from structures B1 to B6 below:

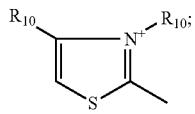 B1

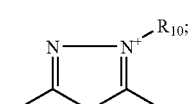 B2

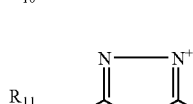 B3

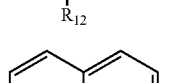 B4

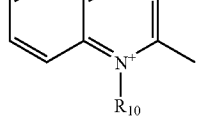 B5

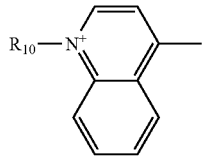 B6

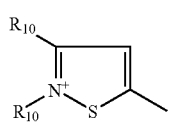

in which $R_{10}$ represents a $C_1$-$C_4$ alkyl radical, $R_{11}$ and $R_{12}$, which may be identical or different, represent a hydrogen atom or a $C_1$-$C_4$ alkyl radical;

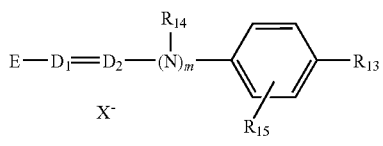
(III)

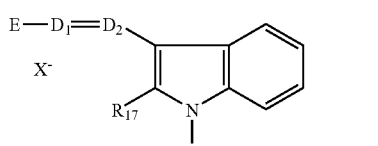
(III')

in which:
$R_{13}$ represents a hydrogen atom, a $C_1$-$C_4$ alkoxy radical, a halogen atom such as bromine, chlorine, iodine or fluorine, or an amino radical,
$R_{14}$ represents a hydrogen atom, a $C_1$-$C_4$ alkyl radical or forms, with a carbon atom of the benzene ring, a heterocycle optionally having oxygen and/or substituted with at least one $C_1$-$C_4$ alkyl group, $R_{15}$ represents a hydrogen atom or a halogen atom such as bromine, chlorine, iodine, or fluorine, $R_{16}$ and $R_{17}$, which may be identical or different, represent a hydrogen atom or a $C_1$-$C_4$ alkyl radical, $D_1$ and $D_2$, which may be identical or different, represent a hydrogen atom or a —CH group, m=0 or 1, it being understood that when $R_{13}$ represents an unsubstituted amino group, then $D_1$ and $D_2$ simultaneously represent a —CH group and m=0, $X^-$ represents an anion that may be chosen from chloride, methyl sulfate, and acetate, E represents a group chosen from structures E1 to E8, below:

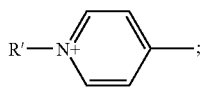
E1

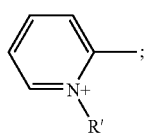
E2

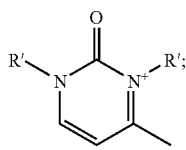
E3

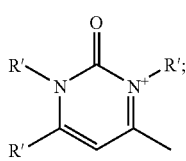
E4

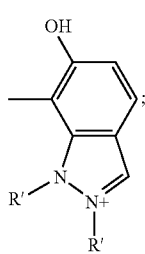
E5

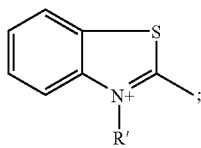
E6

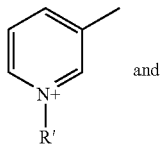
E7 and

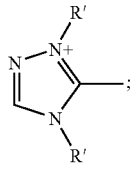
E8 in which R' represents a $C_1$-$C_4$ alkyl radical;

when m=0 and $D_1$ represents a nitrogen atom, then E may also denote a group of structure E9 below:

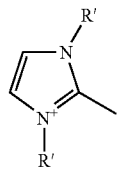
E9 n which R' represents a $C_1$-$C_4$ alkyl radical.

(IV)

in which:

the symbol G represents a group chosen from the structures $G_1$ to $G_3$ below:

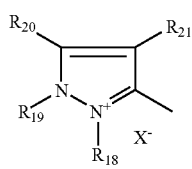
$G_1$

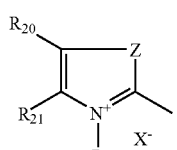
$G_2$

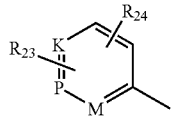
$G_3$ in which structures $G_1$ to $G_3$:

$R_{18}$ denotes a $C_1$-$C_4$ alkyl radical, a phenyl radical which may be substituted with a $C_1$-$C_4$ alkyl radical, or a halogen atom chosen from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy or $NO_2$ radical, or form together in $G_2$ a benzene ring optionally substituted with at least one $C_1$-$C_4$ alkyl, $C_1$-$C_4$ alkoxy, or $NO_2$ radical;

$R_{20}$ may also denote a hydrogen atom;

Z represents an oxygen or sulfur atom or a group —$NR_{19}$;

M represents a group —CH, —CR (R denoting $C_1$-$C_4$ alkyl) or —$NR_{22}(X^-)_r$;

K represents a group —CH, —CR (R denoting $C_1$-$C_4$ alkyl) or —$NR_{22}(X^-)_r$;

P represents a group —CH, —CR (R denoting $C_1$-$C_4$ alkyl) or —$NR_{22}(X^-)_r$;

r denotes 0 or 1;

$R_{22}$ represents an $O^-$ atom, a $C_1$-$C_4$ alkoxy radical or a $C_1$-$C_4$ alkyl radical;

$R_{23}$ and $R_{24}$, which may be identical or different, represent a hydrogen atom or a halogen atom chosen from chlorine, bromine, iodine and fluorine, a $C_1$-$C_4$ alkyl or $C_1$-$C_4$ alkoxy radical, or an —$NO_2$ radical;

—X⁻ represents an anion that may be chosen from chloride, iodide, methyl sulfate, ethyl sulfate, acetate, and perchlorate;

with the proviso that, if $R_{22}$ denotes O⁻, then r denotes zero;

if K or P or M denote —N—(C$_1$-C$_4$)alkyl X⁻, then $R_{23}$ or $R_{24}$ may be different than a hydrogen atom;

if K denotes —NR$_{22}$(X⁻)$_r$, then M=P=—CH, —CR;

if M denotes —NR$_{22}$(X⁻)$_r$, then K=P=—CH, —CR;

if P denotes —NR$_{22}$(X⁻)$_r$, then K=M and denote —CH or —CR;

if Z denotes a sulfur atom with $R_{21}$ denoting C$_1$-C$_4$ alkyl, then $R_{20}$ is other than a hydrogen atom;

if Z denotes —NR$_{22}$ with $R_{19}$ denoting C$_1$-C$_4$ alkyl, then at least one of the radicals $R_{18}$, $R_{20}$ or $R_{21}$ of the group of structure G$_2$ is other than a C$_1$-C$_4$ alkyl radical;

the symbol J represents:

(a) a group of structure J$_1$ below:

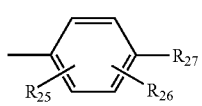

J$_1$ in which structure J$_1$:

$R_{25}$ represents a hydrogen atom, a halogen atom chosen from chlorine, bromine, iodine and fluorine, a C$_1$-C$_4$ alkyl or C$_1$-C$_4$ alkoxy radical, an —OH, —NO$_2$, —NHR$_{28}$, —NR$_{29}$R$_{30}$ or C$_1$-C$_4$-NHCOalkyl radical, or forms with R$_{26}$ a 5- or 6-membered ring optionally having at least one heteroatoms chosen from nitrogen, oxygen, and sulfur;

$R_{26}$ represents a hydrogen atom, a halogen atom chosen from chlorine, bromine, iodine, and fluorine, a C$_1$-C$_4$ alkyl or C$_1$-C$_4$ alkoxy radical, or forms with R$_{27}$ or R$_{28}$ a 5- or 6-membered ring optionally having at least one heteroatom chosen from nitrogen, oxygen, and sulfur;

$R_{27}$ represents a hydrogen atom, an —OH radical, a radical —NHR$_{28}$ or a radical —NR$_{29}$R$_{30}$;

$R_{28}$ represents a hydrogen atom, a C$_1$-C$_4$ alkyl radical, a C$_1$-C$_4$ monohydroxyalkyl, C$_2$-C$_4$ polyhydroxyalkyl radical or a phenyl radical;

$R_{29}$ and $R_{30}$, which may be identical or different, represent a C$_1$-C$_4$ alkyl radical, a C$_1$-C$_4$ monohydroxyalkyl or C$_2$-C$_4$ polyhydroxyalkyl radical;

(b) a 5- or 6-membered nitrogenous heterocyclic group, which may comprise other heteroatoms and/or carbonyl groups and may be substituted with at least one C$_1$-C$_4$ alkyl, amino or phenyl radical, including a group of structure J$_2$ below:

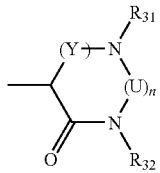

J$_2$ in which structure J$_2$:

$R_{31}$ and $R_{32}$, which may be identical or different, represent a hydrogen atom, a C$_1$-C$_4$ alkyl radical or a phenyl radical;

Y denotes a —CO— radical or a

radical; and n=0 or 1, with, when n denotes 1, U denotes a —CO— radical.

In structures (I) to (IV) defined above, in some embodiments, the C$_1$-C$_4$ alkyl or alkoxy group may denote methyl, ethyl, butyl, methoxy, or ethoxy.

In some embodiments, the compounds of formulae (I) and (III) are:

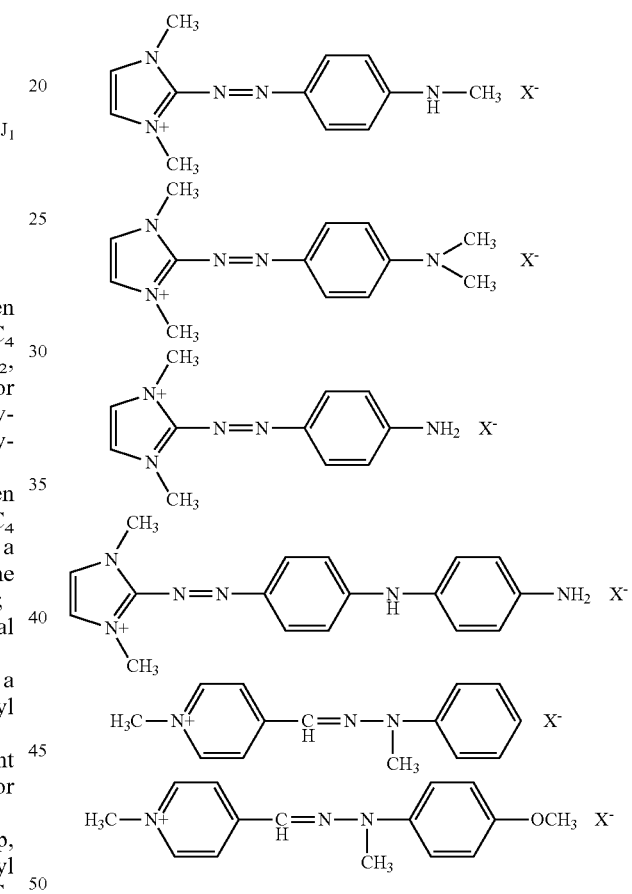

Among the azo direct dyes that may also be mentioned, in a nonlimiting manner, are the following dyes, described in the Colour Index International, 3rd edition:

Disperse Red 17
Basic Red 22
Basic Red 76
Basic Yellow 57
Basic Brown 16
Basic Brown 17
Disperse Black 9.

Mention, in a nonlimiting manner, may also be made of 1-(4'-amino-diphenylazo)-2-methyl-4-bis(β-hydroxyethyl) aminobenzene.

Among the quinone direct dyes that may be mentioned, in a nonlimiting manner, are the following dyes:

Disperse Red 15
Solvent Violet 13

Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-(β,γ-dihydroxypropylamino)anthraquinone.

Among the azine dyes that may be mentioned, in a nonlimiting manner, are the following compounds:
  Basic Blue 17
  Basic Red 2.

Among the triarylmethane dyes, mention, in a nonlimiting manner, may be made of the following compounds:
  Basic Green 1
  Basic Violet 3
  Basic Violet 14
  Basic Blue 7
  Basic Blue 26.

Among the indoamine, mention, in a nonlimiting manner, may be made of the following compounds:
  2-β-hydroxyethylamino-5-[bis(β-4'-hydroxyethyl)amino]anilino-1,4-benzoquinone
  2-β-hydroxyethylamino-5-(2'-methoxy-4'-amino)anilino-1,4-benzoquinone
  3-N-(2'-chloro-4'-hydroxy)phenylacetylamino-6-methoxy-1,4-benzoquinone imine
  3-N-(3'-chloro-4'-methylamino)phenylureido-6-methyl-1,4-benzoquinone imine
  3-[4'-N-(ethyl,carbamylmethyl)amino]phenylureido-6-methyl-1,4-benzoquinone imine.

Among the dyes of tetraazapentamethine type, mention, in a nonlimiting manner, may be made of the following compounds given in the table below:

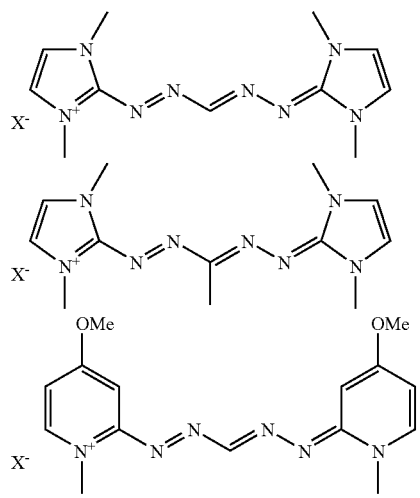

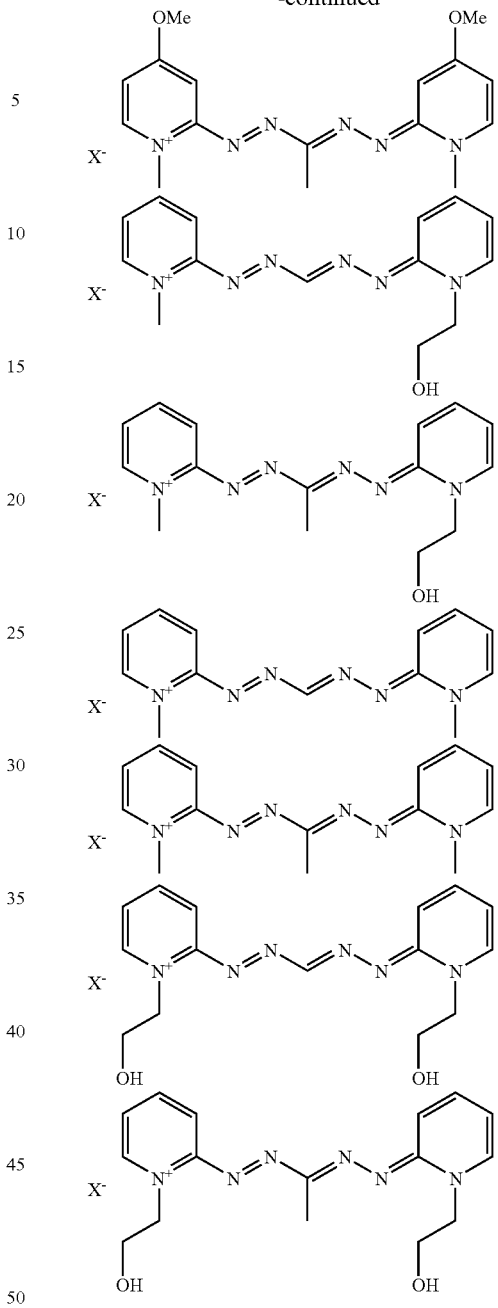

$X^-$ represents an anion chosen from chloride, iodide, methyl sulfate, ethyl sulfate, acetate, and perchlorate.

Among the polychromophoric dyes, mention, in a nonlimiting manner, may be made of symmetrical or nonsymmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group $N(R')_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may be mentioned, in a nonlimiting manner, include 5- or 6-membered rings having 1 to 3 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

Those polychromophores may be, in some embodiments, connected together by means of at least one linker optionally comprising at least one quaternized nitrogen atom that may or may not be engaged in a saturated or unsaturated, optionally aromatic heterocycle.

Exemplary linkers may include, but are not limited to, a linear, branched or cyclic $C_1$-$C_{20}$ alkyl chain, optionally interrupted with at least one heteroatom (such as nitrogen or oxygen) and/or with at least one group comprising such a heteroatom (CO or $SO_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

The bonding between the linker and each chromophore may take place, in some embodiments, via a heteroatom substituent on the phenyl or naphthyl nucleus or via the quaternized nitrogen atom of the cationic heterocycle.

The dye may comprise identical or different chromophores.

As examples of such dyes, reference may be made to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116, and EP 1 671 560.

It is also possible to use the cationic direct dyes mentioned in patent applications: EP 1 006 153, describing dyes comprising two chromophores of anthraquinone type connected via a linker of cationic type; EP 1 433 472, EP 1 433 474, EP 1 433 471 and EP 1 433 473, describing identical or different dichromophoric dyes, connected via a cationic or noncationic linker, and also EP 6 291 333, describing dyes comprising three chromophores, one of them being an anthraquinone chromophore, to which are attached two chromophores of azo or diazacarbocyanin type or an isomer thereof.

Among the natural direct dyes, mention, in a nonlimiting manner, may be made of lawsone, juglone, alizarin, purpurin, carminic acid, kermesic acid, purpurogallin, protocatechaldehyde, indigo, isatin, curcumin, spinulosin, apigenidin and orceins. It is also possible to use extracts or decoctions comprising these natural dyes, such as henna-based poultices or extracts.

In some embodiments, the direct dyes are present in an amount ranging from 0.0001% to 10% by weight relative to the total weight of the composition. In some embodiments, the direct dyes are present in an amount ranging from 0.005% to 5% by weight relative to the total weight of the composition.

Cosmetic composition (B) may comprise one and/or the other types of dyes. In some embodiments, the cosmetic composition (B) may include a mixture of two dye compositions, one comprising at least one oxidation dye, the other comprising at least one direct dye.

In some embodiments, cosmetic composition (B) may additionally comprise at least one organic amine whose $pK_b$ at 25° C. is less than 12.

In some embodiments, the at least one organic amine has a $pK_b$ at 25° C. is less than 12. In some embodiments, the $pK_b$ at 25° C. is less than 6.

In some embodiments, the $pK_b$ corresponds to the function of highest basicity.

In some embodiments, the organic amine may comprise a primary, secondary, or tertiary amine function, and at least one linear or branched $C_1$-$C_a$ alkyl group bearing at least one hydroxyl radical.

Organic amines may be, in some embodiments, chosen from alkanolamines such as mono-, di- or trialkanolamines, comprising one to three identical or different $C_1$-$C_4$ hydroxyalkyl radicals.

Among the compounds of this type that may be mentioned, in a nonlimiting manner, are monoethanolamine, diethanolamine, triethanolamine, monoisopropanolamine, diisopropanolamine, N-dimethylaminoethanolamine, 2-amino-2-methyl-1-propanol, triiso-propanolamine, 2-amino-2-methyl-1,3-propanediol, 3-amino-1,2-propanediol, 3-dimethylamino-1,2-propanediol and tris(hydroxymethylamino)methane.

In some embodiments, the organic amines having the following formula:

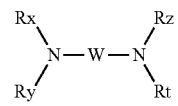

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, may also be suitable for use.

Examples of such amines that may be mentioned include, but are not limited to, 1,3-diaminopropane, 1,3-diamino-2-propanol, spermine, and spermidine.

According to a some embodiments, the organic amine is chosen from amino acids.

The amino acids that may be used are of natural or synthetic origin, in L, D or racemic form, and comprise at least one acid function chosen from carboxylic acid, sulfonic acid, phosphonic acid, and phosphoric acid functions. The amino acids may be in their neutral or ionic form.

As amino acids, mention, in a nonlimiting manner, may be made of aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

In some embodiments, the amino acids may be chosen from basic amino acids comprising an additional amine function optionally included in a ring or in a ureido function.

Such basic amino acids may be chosen, in some embodiments, from those corresponding to formula (I) below:

$$R-CH_2-CH{\overset{NH_2}{\underset{CO_2H}{\diagdown}}} \quad (I)$$

in which R denotes a group chosen from:

—(CH$_2$)$_3$NH$_2$;   —(CH$_2$)$_2$NH$_2$;   —(CH$_2$)$_2$NHCONH$_2$;

$$-(CH_2)_2NH-\underset{\underset{NH}{\|}}{C}-NH_2$$

In some embodiments, the compounds corresponding to formula (I) are histidine, lysine, arginine, ornithine, and citrulline.

In some embodiments, the organic amine is chosen from organic amines of heterocyclic type. Besides histidine that has already been mentioned in the amino acids, mention, in a nonlimiting manner, may be made of pyridine, piperidine, imidazole, triazole, tetrazole, and benzimidazole.

In some embodiments, the organic amine is chosen from amino acid dipeptides. As amino acid dipeptides, mention, in a nonlimiting manner, may be made of carnosine, anserine, and baleine.

In some embodiments, the organic amine is chosen from compounds comprising a guanidine function. Exemplary organic amines include, but are not limited to, guanidine, arginine, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

In some embodiments, the organic amines are chosen from alkanolamines, basic amino acids, and compounds comprising a guanidine function.

Exemplary organic amines include, but are not limited to, alkanolamines chosen from monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

In some embodiments, the organic amines are alkanolamines, such as monoethanolamine.

In some embodiments, cosmetic composition (B) has an organic amine content ranging from 0.01% to 30% by weight relative to the weight of the composition. In some embodiments, cosmetic composition (B) has an organic amine content ranging from 0.1% to 20% by weight relative to the weight of the composition.

In some embodiments, the cosmetic composition (B) may also comprises at least one mineral base.

In some embodiments, the term "mineral compound" may describe any compound bearing in its structure at least one element from columns 1 to 13 of the Periodic Table of the Elements other than hydrogen.

In some embodiments, the mineral base contains at least one element from columns 1 and 2 of the Periodic Table of the Elements other than hydrogen.

In some embodiments, the mineral base has the following structure:

$$(Z_1^{x-})_m(Z_2^{y+})_n$$

in which:
$Z_2$ denotes a metal from columns 1 to 13 of the Periodic Table of the Elements, for instance sodium or potassium;
$Z_1^{x-}$ denotes an anion chosen from $CO_3^{2-}$, $OH^-$, $HCO_3^{2-}$, $SiO_3^-$, $HPO_4^{2-}$, $PO_4^{3-}$ and $B_4O_7^{2-}$ ions;
x denotes 1, 2 or 3;
y denotes 1, 2, 3 or 4;
m and n denote, independently of each other, 1, 2, 3, or 4;
with n*y=m*x.

In some embodiments, the mineral base corresponds to the following formula $(Z_1^{x-})_m(Z_2^{y+})_n$, in which $Z_2$ denotes a metal from columns 1 and 2 of the Periodic Table of the Elements; $Z_1^{x-}$ denotes an anion chosen from $CO_3^{2-}$, $OH^-$ and $SiO_3^{2-}$ ions, x is 1, y denotes 1 or 2, and m and n independently of one another denote 1 or 2, with n*y=m*x.

As mineral bases, mention, in a nonlimiting manner, may be made of sodium carbonate, potassium carbonate, sodium hydroxide, potassium hydroxide, sodium metasilicate, and potassium metasilicate. In some embodiments, the mineral base is an alkali metal carbonate.

In some embodiments, composition (B) has a mineral base content ranging from 0.01% to 30% by weight relative to the weight of the composition. In some embodiments, composition (B) has a mineral base content ranging from 0.1% to 20% by weight relative to the weight of the composition.

In some embodiments, the organic amine whose $pK_b$ is less than 12 at 25° C. and the mineral bases weight ratio ranges from 0.1 to 10.

In some embodiments, the cosmetic composition (B) may be an anhydrous or aqueous composition. the term "aqueous composition" describes a composition comprising more than 5% by weight of water. In some embodiments, the term "aqueous composition" describes a composition comprising more than 10% by weight of water. In some embodiments, the term "aqueous composition" describes a composition comprising more than 20% by weight of water.

In some embodiments, the cosmetic composition (B) is an aqueous composition.

In some embodiments, composition (B) comprises water. In some embodiments, the water concentration ranges from 10% to 90% of the total weight of the composition. In some embodiments, the water concentration ranges from 20% to 80% of the total weight of the composition.

In some embodiments, the composition may further comprise at least one solvent.

Examples of organic solvents that may be mentioned, in a nonlimiting manner, include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

In some embodiments, the at least one solvent is present in an amount ranging from 1% to 40% by weight relative to the weight of the cosmetic composition (B). In some embodiments, the at least one solvent is present in an amount ranging from 5% to 30% by weight relative to the weight of the cosmetic composition (B).

In some embodiments, the cosmetic composition (B) may also comprise standard additives such as those that have been listed previously, and reference may be made thereto.

In some embodiments, the pH of the cosmetic composition (B) in aqueous form, ranges from 2 to 13. In some embodiments, the pH of the cosmetic composition (B) in aqueous form, ranges from 8 to 12. The pH may be adjusted by using additional acidifying or basifying agents, such as those mentioned hereinbelow.

Among the additional acidifying agents that may be mentioned, in a nonlimiting manner, are mineral or organic acids, for instance hydrochloric acid, orthophosphoric acid, sulfuric acid, carboxylic acids, for instance acetic acid, tartaric acid, citric acid or lactic acid, and sulfonic acids.

As regards the additional basifying agent, if it is present, it may be chosen, in some embodiments, from the non-salified organic amines described previously, or optionally aqueous ammonia. In some embodiments, the composition comprises aqueous ammonia or a salt thereof used as additional basifying agent in composition (B), and the aqueous ammonia content is less than or equal to 0.03% by weight of the final composition (expressed as $NH_3$). In some embodiments, the composition comprises aqueous ammonia or a salt thereof used as additional basifying agent in composition (B), and the aqueous ammonia content is less than or equal to 0.01% by weight relative to the final composition. It is indicated that the final composition may result from the mixing of compositions (A), (B), and (C); those mixtures may be prepared either before application to the keratin fibers (extemporaneous preparation) or directly on the keratin fibers (successive applications with or without premixing and without intermediate rinsing).

In some embodiments, aqueous ammonia or its salt is used as additional basifying agent in composition (B), and the content of basifying agents is higher than the content of aqueous ammonia (expressed as $NH_3$).

In some embodiments, the process is performed with a composition (C) comprising at least one oxidizing agent.

In some embodiments, the at least one oxidizing agent is chosen from hydrogen peroxide, urea peroxide, alkali metal bromates or ferricyanides, peroxygenated salts, for instance persulfates, perborates, peracids and precursors thereof, alkali metal or alkaline-earth metal percarbonates, peracids, and precursors thereof.

In some embodiments, at least one redox enzyme such as laccases, peroxidases, and 2-electron oxidoreductases (such as uricase), which may be in the presence of the respective donor or cofactor thereof, may also be used as oxidizing agent.

In some embodiments, the at least one oxidizing agent is formed from hydrogen peroxide in aqueous solution (aqueous hydrogen peroxide solution) whose concentration ranges from 0.1% to 50% by weight relative to the composition (C).

In some embodiments, the at least one oxidizing agent is formed from hydrogen peroxide in aqueous solution (aqueous hydrogen peroxide solution) whose concentration ranges from 0.5% to 20% by weight relative to the composition (C). In some embodiments, the at least one oxidizing agent is formed from hydrogen peroxide in aqueous solution (aqueous hydrogen peroxide solution) whose concentration ranges from 1% to 15% by weight relative to the composition (C).

Depending on the desired degree of lightening, the oxidizing agent may also comprise an oxidizing agent chosen from, for instance, peroxygenated salts.

The composition (C) may or may not be aqueous. In some embodiments, the term "aqueous composition" describes a composition comprising more than 5% by weight of water. In some embodiments, the term "aqueous composition" describes a composition comprising more than 10% by weight of water. In some embodiments, the term "aqueous composition" describes a composition comprising more than 20% by weight of water.

In some embodiments, composition (C) is an aqueous composition.

In some embodiments, composition (C) further comprises at least one organic solvent.

Examples of organic solvents that may be mentioned, in a nonlimiting manner, include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

In some embodiments, the at least one solvent is present in an amount ranging from 1% to 40% by weight of the cosmetic composition (C). In some embodiments, the at least one solvent is present in an amount ranging from 5% to 30% by weight of the composition (C).

In some embodiments, composition (C) may further comprise at least one acidifying agent.

Among the acidifying agents, examples that may be mentioned, in a nonlimiting manner, include mineral or organic acids, for instance hydrochloric acid, orthophosphoric acid, sulfuric acid, carboxylic acids, for instance acetic acid, tartaric acid, citric acid or lactic acid, and sulfonic acids.

In some embodiments, the pH of composition (C), which is aqueous, is less than 7.

The composition (C) may also contain, in some embodiments, other ingredients such as those detailed previously in the context of the anhydrous composition (A).

In some embodiments, composition (C) is in the form of a solution, an emulsion, or a gel.

In some embodiments, the composition resulting from mixing together compositions (A), (B), and (C) is free of aqueous ammonia.

In some embodiments, the composition resulting from mixing together compositions (A), (B), and (C) comprises fatty substances in a content higher than 20% by weight. In some embodiments, the composition resulting from mixing together compositions (A), (B), and (C) comprises fatty substances in a content higher than 25% by weight. In some embodiments, the composition resulting from mixing together compositions (A), (B), and (C) comprises fatty substances in a content higher than 30% by weight.

In some embodiments, compositions (A), (B), and (C) are applied to wet or dry keratin fibers, successively and without intermediate rinsing. In some embodiments, compositions (A) then (B) and then (C) are applied to wet or dry keratin fibers, successively and without intermediate rinsing. In some embodiments, compositions (B) then (A) and then (C) are applied to wet or dry keratin fibers, successively and without intermediate rinsing.

In some embodiments, the composition resulting from the mixing, before application, of compositions (A) and (B), and then composition (C), are successively applied and without intermediate rinsing.

In some embodiments, a composition obtained by extemporaneous mixing, before application, of compositions (A), (B) and (C) is applied to the wet or dry keratin fibers.

In some embodiments, the weight ratios R1 of the amounts of compositions (A)+(B)/(C) and R2 of the amounts of compositions (A)/(B) range from 0.1 to 10. In some embodiments, the weight ratios R1 of the amounts of compositions (A)+(B)/(C) and R2 of the amounts of compositions (A)/(B) range from 0.3 to 3.

In some embodiments, the mixture present on the fibers (resulting either from the extemporaneous mixing of the compositions, or from the successive application of these compositions) is left in place for a time ranging from about 1 minute to 1 hour. In some embodiments, the mixture present on the fibers (resulting either from the extemporaneous mixing of the compositions, or from the successive application of these compositions) is left in place for a time ranging from about 5 minutes to 30 minutes.

In some embodiments, the temperature during the process ranges from room temperature (for example, ranging from 15 to 25° C.) to 80° C. In some embodiments, the temperature during the process ranges from room temperature (for example, ranging from 15 to 25° C.) to 60° C.

In some embodiments, after the treatment, the human keratin fibers are optionally rinsed with water, optionally washed with a shampoo, and then rinsed with water, before being dried or left to dry.

Also provided is an anhydrous composition comprising at least one fatty substance, at least one surfactant, at least one organic amine with a $pK_b$ of less than 12 at 25° C., and at least one mineral base other than aqueous ammonia.

In some embodiments, the anhydrous composition comprises at least one fatty substance, at least one surfactant, at least one organic amine with a $pK_b$ of less than 12 at 25° C. and at least one mineral base chosen from sodium carbonate, potassium carbonate, sodium hydroxide, potassium hydroxide, sodium metasilicate, and potassium metasilicate.

In some embodiments, the at least one mineral base used in the anhydrous composition is chosen from alkali metal carbonates.

Also provided is a multi-compartment device comprising a first compartment having the anhydrous composition (A) comprising at least one fatty substance and at least one surfactant, a second compartment having a cosmetic composition (B) comprising at least one organic amine with a $pK_b$ of less than 12 at 25° C., and at least one mineral base, and also optionally at least one oxidation dye, at least one direct dye, or both, and a third compartment having a composition (C) comprising at least one oxidizing agent.

The examples that follow serve to illustrate the invention without, however, being limiting in nature.

EXAMPLES

Dyeing Process

Example 1

The following compositions were prepared (amounts expressed in grams).

Anhydrous Composition A:

| | |
|---|---|
| Oxyethylenated (4 EO) sorbitan monolaurate | 21.7 |
| Fumed silica of hydrophobic nature | 11.1 |
| Liquid petroleum jelly | qs 100 |

Cosmetic Composition B:

| | |
|---|---|
| Potassium carbonate | 7.25 |
| Monoethanolamine | 9.50 |
| para-Phenylenediamine | 2.35 |
| Resorcinol | 2.37 |
| Sodium metabisulfite powder | 0.70 |
| Erythorbic acid | 0.25 |
| Diethylenetriaminepentaacetic acid, pentasodium salt, as an aqueous 40% solution | 1 |
| Ethanol | 8.80 |
| Propylene glycol | 6.20 |
| Hexylene glycol | 3.00 |
| Dipropylene glycol | 3.00 |
| Demineralized water | qs 100 |

At the time of use, the following were mixed together:
10 parts by weight of composition (A),
4 parts by weight of composition (B), and
15 parts by weight of an aqueous oxidizing composition comprising 6% by weight of hydrogen peroxide at pH 2.3 and comprising about 80% water.

The mixture obtained, the pH of which was about 10, was then applied to a lock of natural hair having 90% grey hairs (NG) and to a lock of permanent-waved hair having 90% grey hairs (PWG). The bath ratio "mixture/lock" was, respectively, 10/1 (g/g).

The leave-on time was 30 minutes at 27° C. After this time, the locks were rinsed, and then washed with Elsève multivitamin shampoo.

Results

The color of the locks was evaluated in the CIE L*a*b* system using a Minolta CM2600D spectrophotometer.

a. Calculation of the Rise or Variation in Color ($\Delta E_{ab}^*$)

The rise in coloration ($\Delta E_{ab}^*$) was evaluated in the CIE L*a*b* system using a Minolta CM2600D spectrophotometer. In this L*a*b* system, L* represents the intensity of the color, a* represents the green/red color axis and b* represents the blue/yellow color axis. The lower the value of L*, the darker or more intense the color.

In the table below, the value of $\Delta E_{ab}^*$ was calculated from the values of L*a*b* according to the following equation (i):

$$\Delta E_{ab}^* = \sqrt{(L^* - L_o^*)^2 + (a^* - a_o^*)^2 + (b^* - b_o^*)^2} \quad (i)$$

The rise in coloration ($\Delta E_{ab}^*$) was calculated on the locks of natural grey hair (NG) and on the locks of permanent-waved grey hair.

In equation (i), for the locks of natural grey hair (NG), L*, a* and b* represent the values measured on locks of natural grey hair after coloration, and $L_o^*$, $a_o^*$ and $b_o^*$ represent the values measured on undyed natural grey hair.

In equation (i), for the locks of permanent-waved grey hair (PWG), L*, a* and b* represent the values measured on locks of permanent-waved grey hair after dyeing, and $L_o^*$, $a_o^*$ and $b_o^*$ represent the values measured on locks of undyed permanent-waved grey hair.

The greater the value of $\Delta E_{ab}^*$, the better the rise or variation of the color.

b. Calculation of the Selectivity

The value of ΔE (selectivity) was also calculated from the values of L*, a* and b* measured according to the following equation (ii):

$$\Delta E = \sqrt{(L^* - L_o^*)^2 + (a^* - a_o^*)^2 + (b^* - b_o^*)^2} \quad \text{(ii)}$$

In equation (ii), L*, a* and b* represent the values measured on dyed natural grey hair, and $L_o^*$, $a_o^*$ and $b_o^*$ represent the values measured on locks of dyed permanent-waved grey hair.

The coloration selectivity ΔE corresponds to the variation in color between natural hair, representative of the nature of the hair at the root, and permanent-waved hair, which is representative of the nature of the hair at the end. The lower the value of ΔE, the more uniform the coloration between the end and the root of the hair.

The results are given in the table below.

|  | L* | a* | b* | $\Delta E_{ab}^*$ | ΔE selectivity |
|---|---|---|---|---|---|
| Lock of untreated natural hair | 58.0 | 0.3 | 12.2 |  |  |
| Lock of untreated permanent-waved hair | 61.8 | −0.01 | 13.3 |  |  |
| Lock of natural hair treated with the composition described herein | 19.2 | 2.1 | 5.2 | 39.5 | 1.3 |
| Lock of permanent-waved hair treated with the composition described herein | 18.3 | 1.8 | 4.3 | 44.5 |  |

As seen in the above table, strong and sparingly selective coloration was obtained with the process described herein.

Furthermore, no aggressive odor was observed, either during the preparation of the dye mixture, or during the leave-on time on the locks.

Example 2

The following compositions were prepared (amounts expressed in grams).

Anhydrous Composition A:

| Oxyethylenated (4 EO) sorbitan monolaurate | 21.7 |
|---|---|
| Fumed silica of hydrophobic nature | 11.1 |
| Liquid petroleum jelly | qs 100 |

Cosmetic Composition B:

| Potassium carbonate | 7.25 |
|---|---|
| Monoethanolamine | 9.50 |
| para-Phenylenediamine | 2.39 |
| 4-Amino-2-hydroxytoluene | 2.68 |
| Sodium metabisulfite | 0.70 |
| Erythorbic acid | 0.25 |
| Diethylenetriaminepentaacetic acid, pentasodium salt, as an aqueous 40% solution | 1 |
| Ethanol | 8.80 |
| Propylene glycol | 6.20 |
| Hexylene glycol | 3.00 |
| Dipropylene glycol | 3.00 |
| Demineralized water | qs 100 |

At the time of use, the following were mixed together:
10 parts by weight of composition (A),
4 parts by weight of composition (B), and
15 parts by weight of an aqueous oxidizing composition comprising 6% by weight of hydrogen peroxide at pH 2.3 and comprising about 80% water.

The mixture obtained, the pH of which is about 10, was then applied to a lock of natural hair having 90% grey hairs (NG) and to a lock of permanent-waved hair having 90% grey hairs (PWG). The bath ratio "mixture/lock" was, respectively, 10/1 (g/g).

The leave-on time was 30 minutes at 27° C. After this time, the locks were rinsed, and then washed with Elsève multivitamin shampoo.

Results

The color of the locks was evaluated in the CIE L*a*b* system using a Minolta CM2600D spectrophotometer.

a. Calculation of the Rise or Variation in Color ($\Delta E_{ab}^*$)

The rise in coloration ($\Delta E_{ab}^*$) was evaluated in the CIE L*a*b* system using a Minolta CM2600D spectrophotometer according to equation (i) described above.

b. Calculation of the Selectivity

The value of ΔE (selectivity) was also calculated from the values of L*, a* and b* measured according to equation (ii) described above.

The results are given in the table below.

|  | L* | a* | b* | $\Delta E_{ab}^*$ | ΔE selectivity |
|---|---|---|---|---|---|
| Lock of untreated natural hair | 58.0 | 0.3 | 12.2 |  |  |
| Lock of untreated permanent-waved hair | 61.8 | −0.01 | 13.3 |  |  |
| Lock of natural hair treated with the composition described herein | 17.0 | 9.3 | −0.1 | 43.7 | 2.2 |
| Lock of permanent-waved hair treated with the composition described herein | 17.1 | 7.1 | 0.1 | 47.2 |  |

As shown by the above table, a strong and sparingly selective violet color was obtained with the process described herein.

Furthermore, no aggressive odor was observed, either during the preparation of the dye mixture, or during the leave-on time on the locks.

Lightening Process

Example

The following compositions were prepared (the amounts are expressed in grams, unless otherwise mentioned):

Anhydrous Composition (A):

| Oxyethylenated (4 EO) sorbitan monolaurate | 21.7 |
|---|---|
| Fumed silica of hydrophobic nature | 11.1 |
| Liquid petroleum jelly | qs 100 |

Cosmetic Composition B:

| Potassium carbonate | 7.25 |
|---|---|
| Monoethanolamine | 9.50 |
| Demineralized water | qs 100 |

At the time of use, the following were mixed together:
10 parts by weight of the anhydrous composition (A),
4 parts by weight of the cosmetic composition (B), and 15 parts by weight of aqueous oxidizing composition (C) comprising 6% hydrogen peroxide at pH 2.3.

The mixture obtained, the pH of which is about 9, was then applied to a natural chestnut-colored lock (tone depth of 3). The bath ratio "mixture/lock" was, respectively, 10/1 (g/g).

The leave-on time was 30 minutes at 27° C. After this time, the locks were rinsed, and then washed with Elsève multivitamin shampoo.

A good level of lightening was obtained, without any aggressive odor being given off.

For comparative purposes, the comparative composition 1 based on aqueous ammonia was prepared (unless otherwise mentioned, the amounts were also expressed in grams).
Comparative Composition 1:

| | |
|---|---|
| Oleyl alcohol polyglycerolated with 2 mol of glycerol | 4 |
| Oleyl alcohol polyglycerolated with 4 mol of glycerol | 5.69 AM |
| Oleic acid | 3 |
| Oleylamine with 2 mol of ethylene oxide, sold under the trade name Ethomeen 012 by the company Akzo | 7 |
| Diethylaminopropyl laurylaminosuccinamate, sodium salt, at 55% active material | 3.0 AM |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Ammonium acetate | 0.8 |
| Aqueous ammonia having 20% NH$_3$ (including 41.15% NH$_4$OH) | 10.2 |
| Demineralized water qs | 100 g |

At the time of use, the comparative composition 1 was mixed on a weight-for-weight basis with an aqueous oxidizing composition comprising 6% by weight of hydrogen peroxide at pH 2.3.

The mixture thus obtained, the pH of which was approximately equal to 9, was then applied to a natural chestnut-brown lock (tone depth of 3). The bath ratio "mixture/lock" was, respectively, 10/1 (g/g).

The leave-on time was 30 minutes at 27° C. After this leave-on time, the lock was rinsed and then washed with Elsève multivitamin shampoo.

The use of the process described herein (Example 1) did not cause the release of any aggressive odor, in contrast with the use of the process with the comparative composition 1, which gave off a strong odor of ammonia.

What is claimed is:

1. A process for lightening or dyeing keratin fibers, comprising applying to the fibers:
   (a) an anhydrous cosmetic composition (A) comprising at least one fatty substance and at least one surfactant,
   (b) a cosmetic composition (B) comprising at least one organic amine with a pK$_b$ of less than 12 and at least one mineral base, and
   (c) a composition (C) comprising at least one oxidizing agent;
   wherein when the process is a process for dyeing keratin fibers, then composition (B) further comprises at least one oxidation dye, at least one direct dye, or a mixture thereof.

2. A process according to claim 1, wherein the anhydrous cosmetic composition (A) comprises less than 5% by weight of water.

3. A process according to claim 1, wherein the at least one fatty substance is chosen from compounds that are liquid or pasty at room temperature and at atmospheric pressure.

4. A process according to claim 1, wherein the at least one fatty substance is chosen from $C_6$-$C_{16}$ lower alkanes, fatty alcohols, fatty acid esters, fatty alcohol esters, non-silicone oils of mineral origin of more than 16 carbon atoms, or of plant or synthetic origin, non-silicone waxes, and silicones.

5. A process according to claim 1, wherein the at least one fatty substance is chosen from liquid petroleum jelly, polydecenes, and liquid esters of fatty acids or of fatty alcohols, and mixtures thereof.

6. A process according to claim 1, wherein anhydrous composition (A) comprises at least one surfactant chosen from nonionic surfactants.

7. A process according to claim 1, wherein the organic amine has a pK$_b$ of less than 10.

8. A process according to claim 1, wherein the at least one organic amine is chosen from alkanolamines.

9. A process according to claim 1, wherein the at least one mineral base is chosen from sodium carbonate, potassium carbonate, sodium hydroxide, potassium hydroxide, sodium metasilicate, and potassium metasilicate.

10. A process according to claim 1, wherein the at least one mineral base is chosen from alkali metal carbonates.

11. A process according to claim 1, wherein the at least one organic amine with a pK$_b$ of less than 12 at 25° C./at least one mineral base weight ratio ranges from 0.1 to 10.

12. A process according to claim 1, wherein compositions (A), (B) and (C), are applied successively and without intermediate rinsing.

13. A process according to claim 1, wherein the composition resulting from the mixing, before application, of compositions (A) and (B) and then the composition (C) is applied successively and without intermediate rinsing, or in that a composition obtained by extemporaneous mixing, before application, of compositions (A), (B), and (C), is applied.

14. An anhydrous composition comprising at least one fatty substance, at least one surfactant, at least one organic amine with a pK$_b$ of less than 12 at 25° C., and at least one mineral base other than aqueous ammonia.

15. A multi-compartment device comprising a first compartment having the anhydrous composition (A) according to claim 1, a second compartment having a composition (B) according to claim 1, and a third compartment having a composition (C) having at least one oxidizing agent.

* * * * *